(12) United States Patent
Choe et al.

(10) Patent No.: US 7,727,236 B2
(45) Date of Patent: Jun. 1, 2010

(54) INSTRUMENTATION FOR FIXATION DEVICES

(75) Inventors: Simon H. Choe, Hoboken, NJ (US); Ross T Leung, Piscataway, NJ (US)

(73) Assignee: EBI, LLC, Parsippany, NJ (US)

( * ) Notice: Subject to any disclaimer, the term of this patent is extended or adjusted under 35 U.S.C. 154(b) by 769 days.

(21) Appl. No.: 11/439,419

(22) Filed: May 23, 2006

(65) Prior Publication Data
US 2007/0276401 A1    Nov. 29, 2007

(51) Int. Cl.
*A61B 17/56* (2006.01)
(52) U.S. Cl. .................... 606/86 R; 606/96
(58) Field of Classification Search ............ 606/80, 606/96, 104
See application file for complete search history.

(56) References Cited

U.S. PATENT DOCUMENTS

| | | | |
|---|---|---|---|
| 3,128,768 A | 4/1964 | Geistauts | |
| 3,765,034 A | 10/1973 | Johnston | |
| 3,892,232 A | 7/1975 | Nuefeld | |
| 4,549,538 A | 10/1985 | Schadrack, III et al. | |
| 5,049,150 A | 9/1991 | Cozad | |
| 5,405,348 A | 4/1995 | Anspach, Jr. et al. | |
| 5,507,801 A | 4/1996 | Gisin et al. | |
| 5,649,931 A * | 7/1997 | Bryant et al. | 606/104 |
| 5,971,988 A | 10/1999 | Reccius et al. | |
| 6,238,400 B1 | 5/2001 | Bays | |
| 6,332,886 B1 | 12/2001 | Green et al. | |
| 6,391,017 B2 | 5/2002 | Bays | |
| 6,635,067 B2 * | 10/2003 | Norman | 606/180 |
| 6,673,076 B2 | 1/2004 | Delogé et al. | |
| 6,746,453 B2 | 6/2004 | Delogé et al. | |
| 6,783,533 B2 | 8/2004 | Green et al. | |
| 6,916,323 B2 | 7/2005 | Kitchens | |
| 6,926,720 B2 | 8/2005 | Castañeda | |
| 6,951,562 B2 | 10/2005 | Zwirnmann | |
| 2004/0092940 A1 * | 5/2004 | Zwirnmann | 606/80 |
| 2005/0059975 A1 * | 3/2005 | Fanger et al. | 606/80 |
| 2005/0085824 A1 | 4/2005 | Castaneda | |
| 2005/0085825 A1 * | 4/2005 | Castaneda | 606/102 |
| 2007/0270771 A1 * | 11/2007 | Ralph et al. | 604/317 |

OTHER PUBLICATIONS

PCT International Search Report And The Written Opinion Of The International Searching Authority mailed May 19, 2008 for PCT/US07/11796.

* cited by examiner

*Primary Examiner*—Eduardo C Robert
*Assistant Examiner*—Elana B Fisher
(74) *Attorney, Agent, or Firm*—Harness, Dickey

(57) ABSTRACT

An instrument assembly for bone drilling. The instrument assembly can include a soft tissue sleeve defining an internal channel, and an irrigation cap removably coupled to the sleeve. The irrigation cap can include a delivery port connectable to an irrigation source for delivering irrigation to the internal channel, the port in fluid communication with the internal channel.

7 Claims, 9 Drawing Sheets

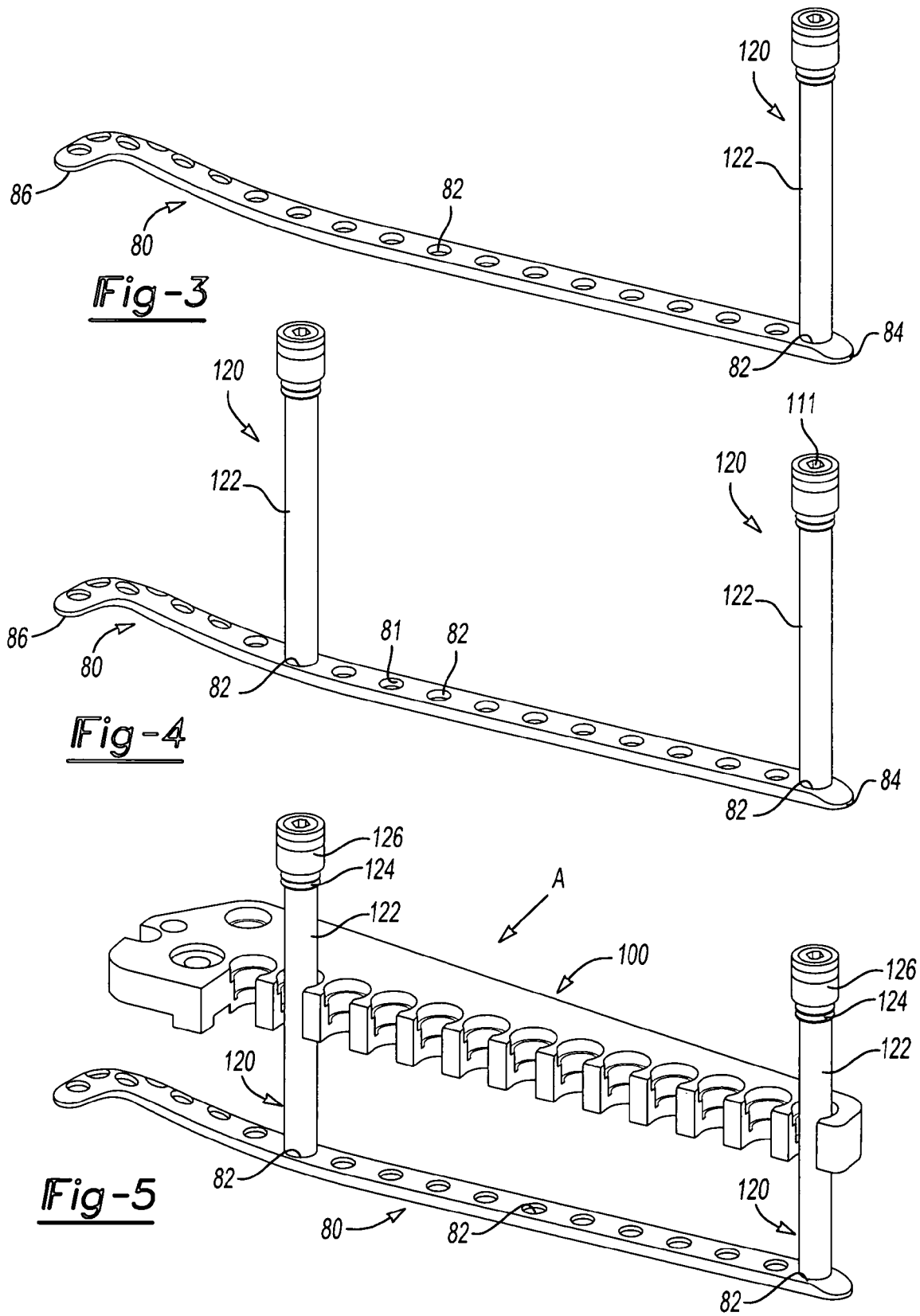

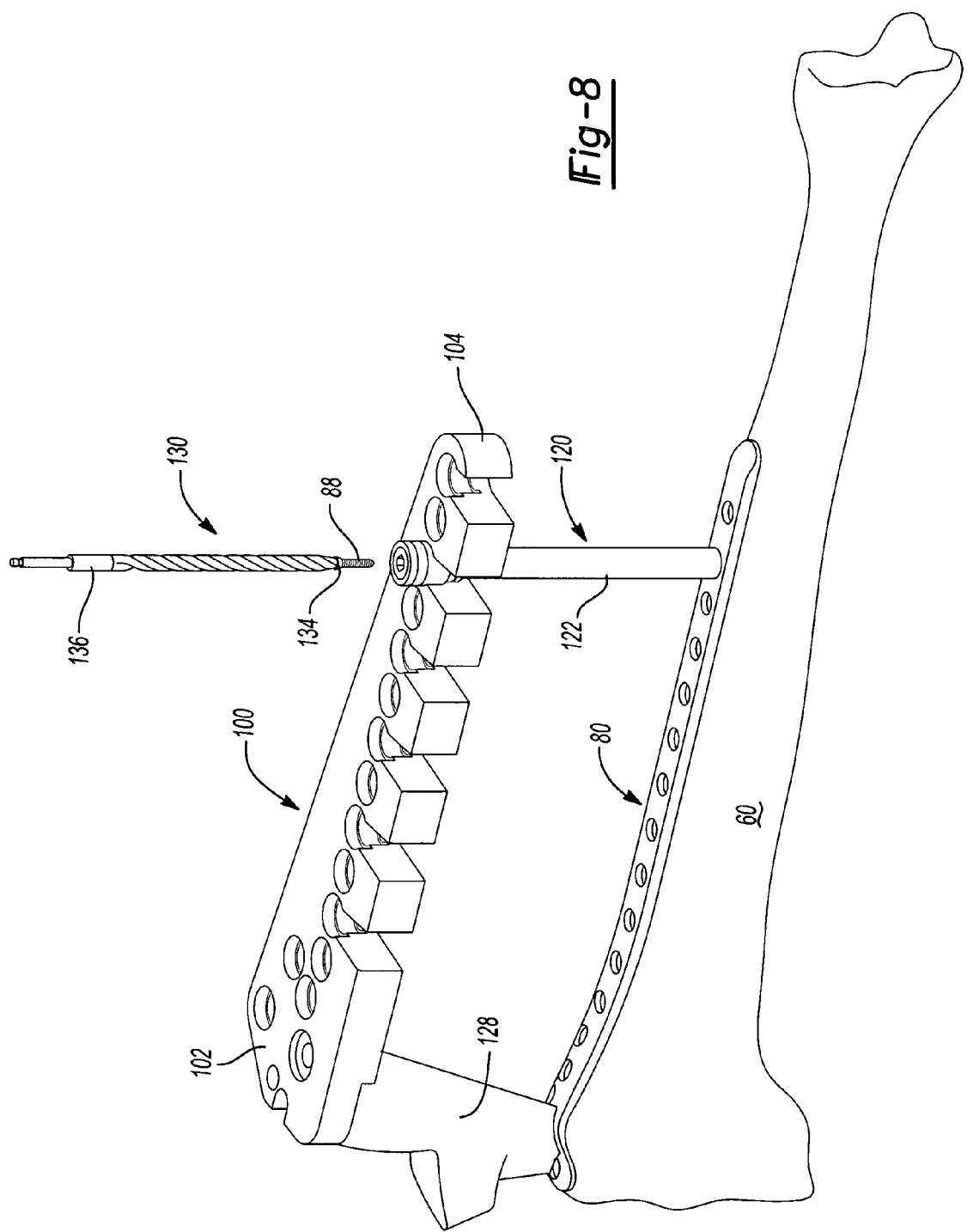

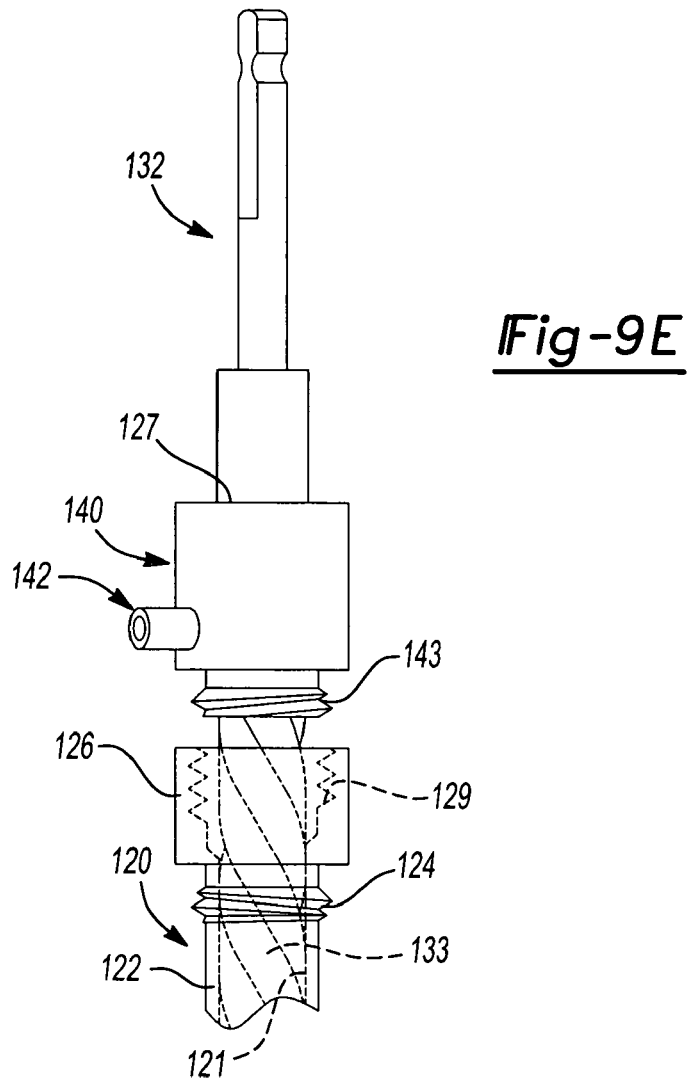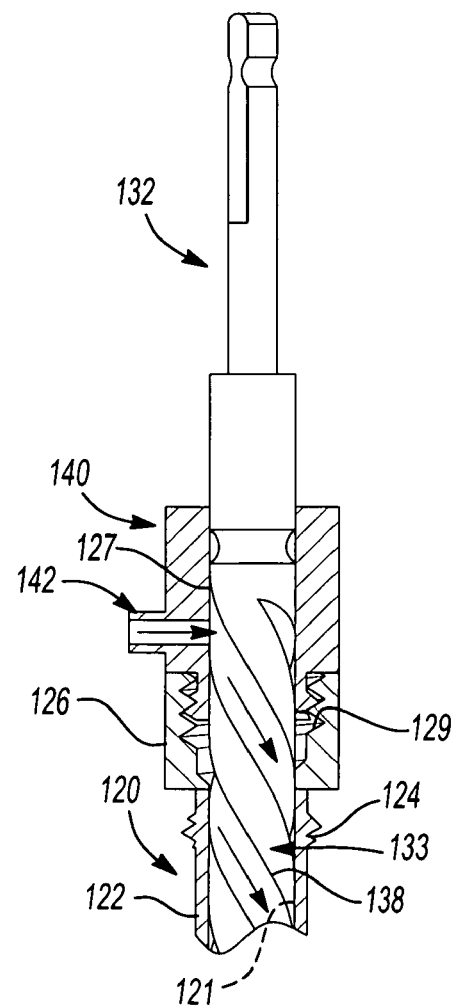
Fig-9E
Fig-9F

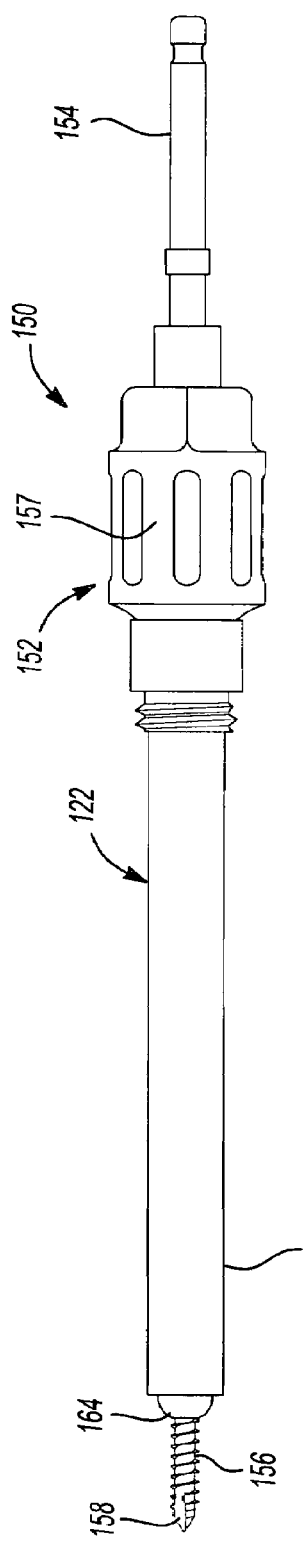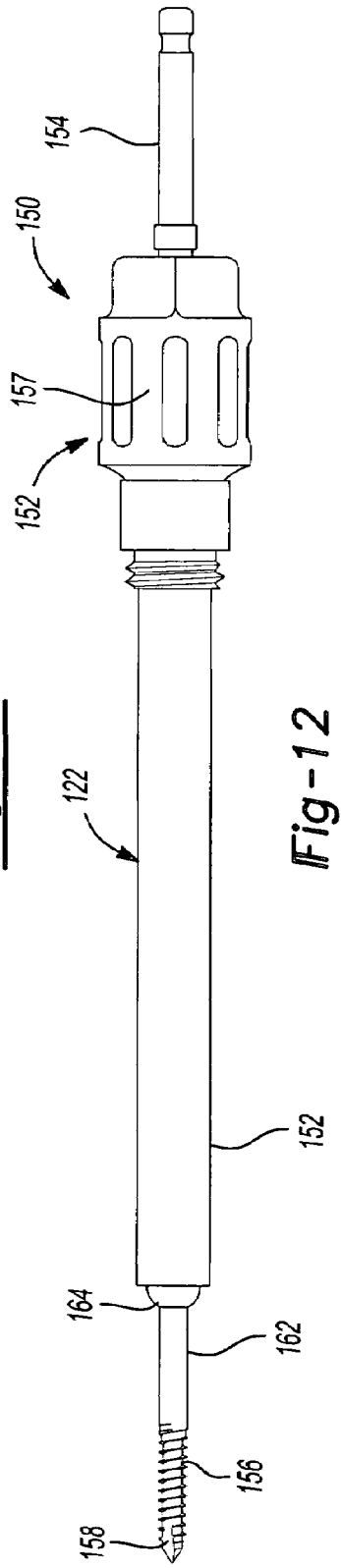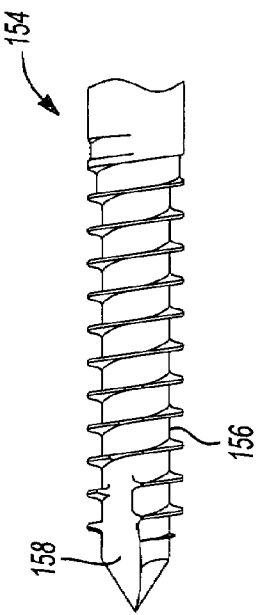
Fig-11
Fig-12
Fig-13

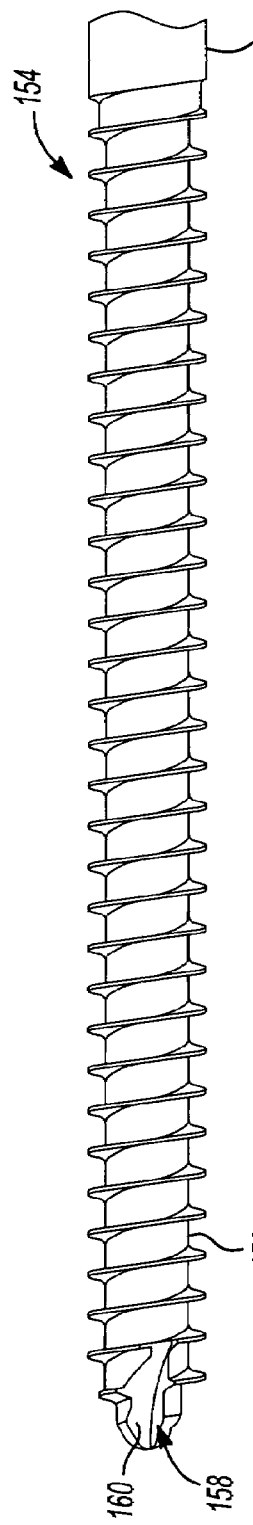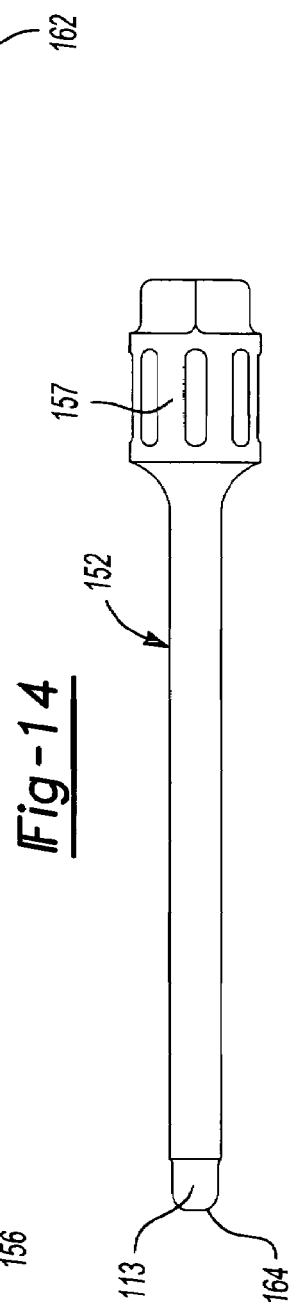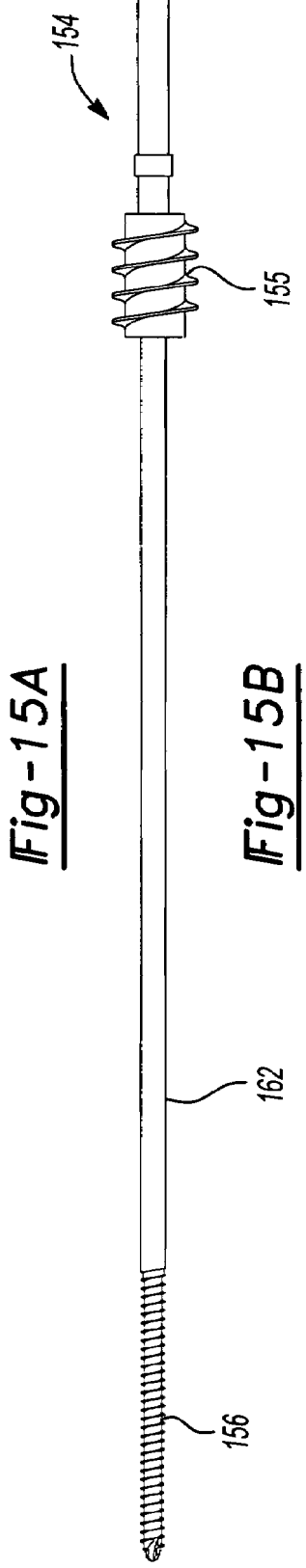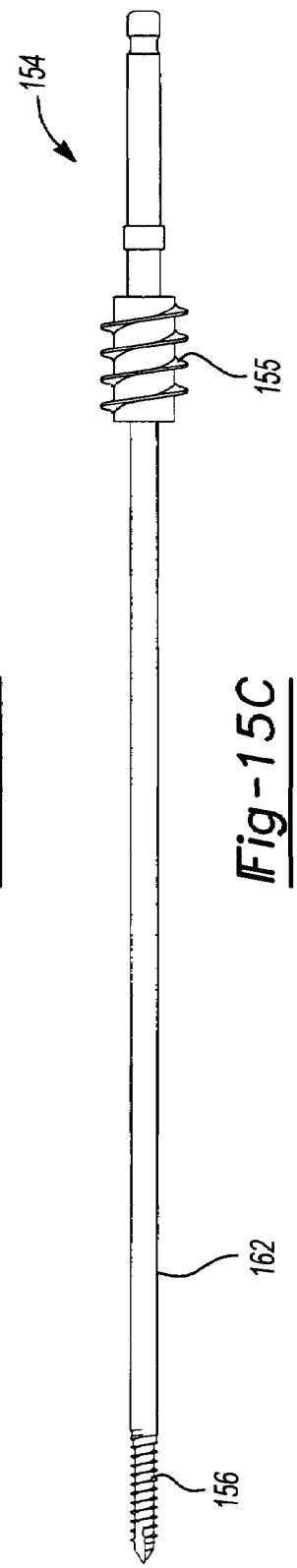
Fig-14
Fig-15A
Fig-15B
Fig-15C

INSTRUMENTATION FOR FIXATION DEVICES

Various instruments are known for use in surgical procedures affixing internal fixation plates to bone portions. Such devices can include, for example, targeting jigs for the fixation plates, irrigation instruments for use with bone drilling, and push-pull reduction devices.

It is still desirable to have improved instruments that can be used selectively together or separately with ease and without requiring extensive disassembly and re-assembly during the surgical procedures.

SUMMARY

According to one aspect, the present teachings provide an instrument assembly for bone drilling. The instrument assembly can include a soft tissue sleeve defining an internal channel, and an irrigation cap removably coupled to the sleeve. The irrigation cap can include a delivery port connectable to an irrigation source for delivering irrigation to the internal channel, the port in fluid communication with the internal channel.

According to another aspect, the present teachings provide a temporary fixator for an internal fixation device including a tubular component defining an internal bore, and a shaft having a bone-gripping tip. The shaft can be threadably coupled with the bore of the tubular component.

According to another aspect, the present teachings provide an instrument assembly for internal bone fixation including a driver having helical irrigation grooves, a temporary fixator, a soft tissue sleeve having an internal channel, and an irrigation cap. The temporary fixator can include a tubular component and a shaft with a bone-gripping tip received in the tubular component. The tubular component can have a spherical tip for contacting an inner wall of a hole of an internal fixation device. The channel of the soft tissue sleeve can be configured to receive selectively the driver and the temporary fixator. The irrigation cap can include a delivery port for connection to an irrigation source and can be removably connected to the soft tissue sleeve when the driver is received in the soft tissue sleeve.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 3-7 illustrate an exemplary procedure for using the targeting device of FIG. 2;

FIG. 8 is an isometric environmental view of an exemplary irrigation assembly according to the present teachings shown in use with a targeting device and a fixation device;

FIGS. 9E and 9F are detailed views illustrating an exemplary connection of the irrigation cap and the soft tissue sleeve according to the present teachings;

FIG. 11 is a plan view of an exemplary temporary fixator according to the present teachings, the temporary fixator shown with a soft tissue protective sleeve;

FIG. 12 is a plan view of an exemplary temporary fixator according to the present teachings, the temporary fixator shown with a soft tissue protective sleeve;

FIG. 13 is a plan view of a detail of a drill shaft of the temporary fixator of FIG. 11;

FIG. 14 is a plan view of a detail of a drill shaft of the temporary fixator of FIG. 12;

FIG. 15A is a plan view of an exemplary tubular component for the temporary fixators of FIGS. 11 and 12;

FIG. 15B is a plan view of a drill shaft of the temporary fixator of FIG. 11; and FIG. 15C is a plan view of a drill shaft of the temporary fixator of FIG. 12.

DESCRIPTION OF VARIOUS ASPECTS

The following description is merely exemplary in nature and is in no way intended to limit the invention, its application, or uses. For example, although the instruments of present teachings are illustrated in association with a particular fixation device (i.e. for the proximal tibia), the instruments can be used in other applications, including but not limited to applications in connection with other internal fixation devices.

Figure 1:
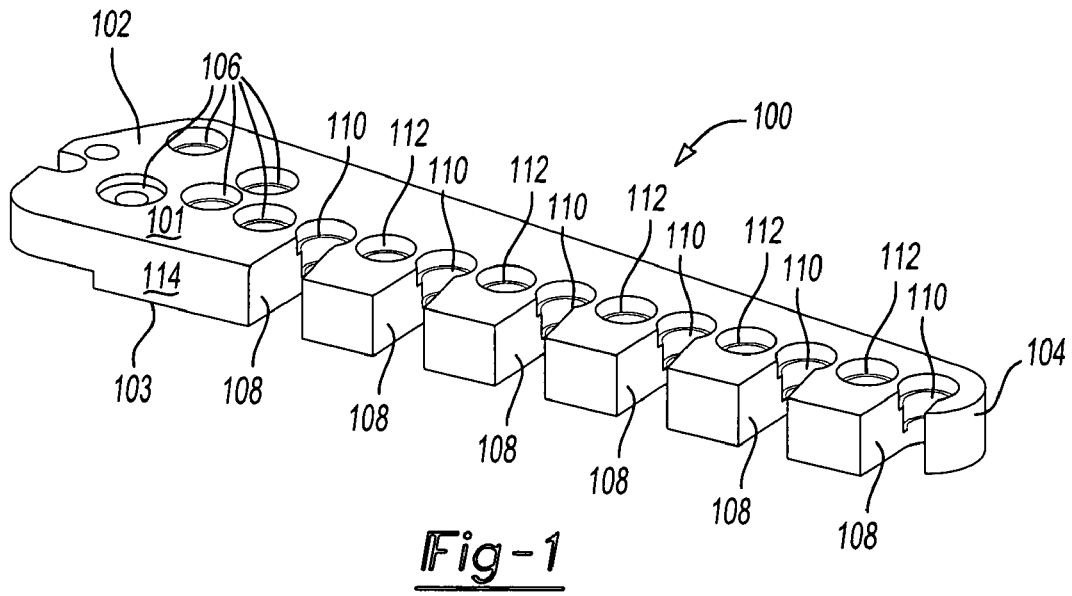
FIG. 1 is an isometric view of an exemplary targeting device according to the present teachings.
Figure 2:
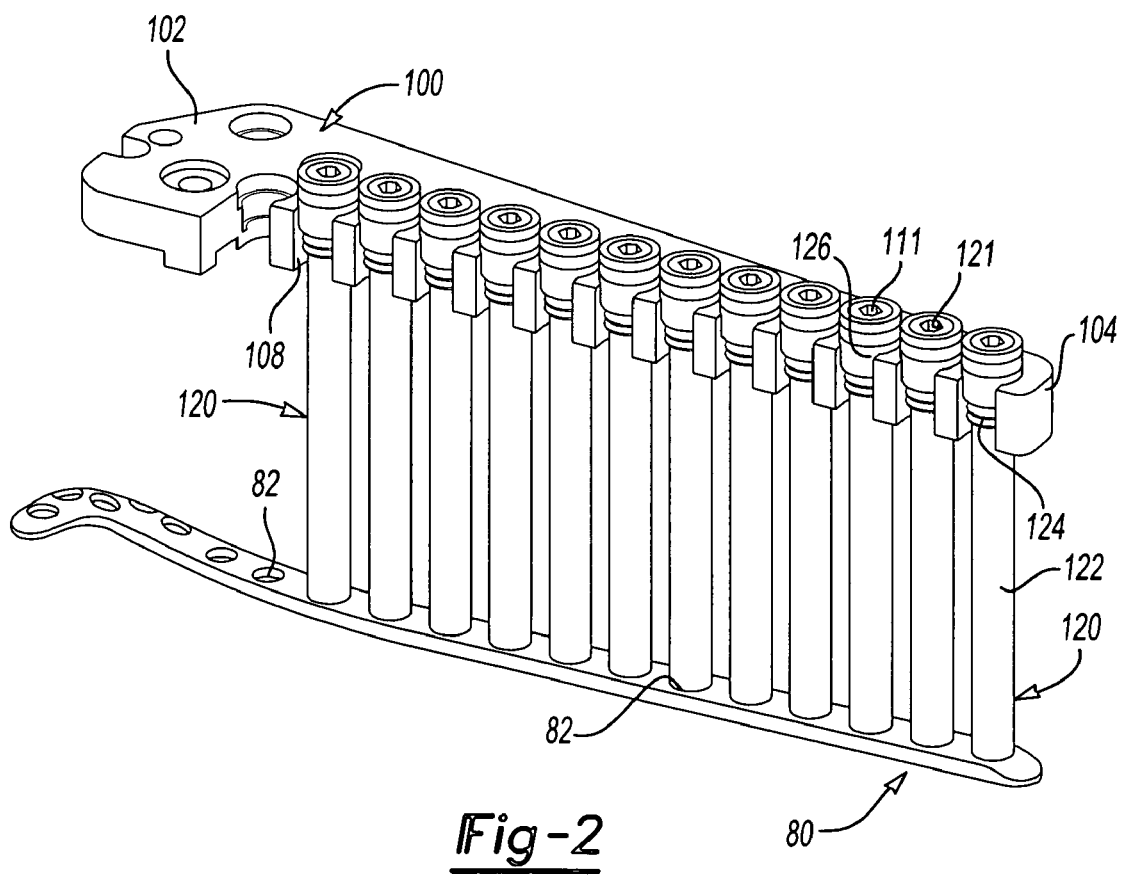
FIG. 2 is an isometric environmental view an exemplary targeting device according to the present teachings shown with a fixation device and soft tissue guide assemblies.

Referring to FIG. 1, an exemplary targeting device 100 according to the present teachings is illustrated. The targeting device 100 can be plate-like with an upper surface 101, a lower surface 103, a first or proximal end 102 and a second or distal end 104. The targeting device 100 can include adjacent the proximal end 102 one or more holes 106 extending through the thickness of the targeting device 100 from the upper surface 101 to the lower surface 102 and adapted to receive drill guides, protective sleeves, drills or other instruments. The targeting device 100 can include a series of through-holes 112 adjacent a side surface 114 that extends between the proximal end 102 and the distal end 104 of the targeting device. The targeting device 100 can also include a series of side-entry slots 108 defined along the side surface 114 and open from the side surface 114. Each of the side-entry slots 108 can include a portion defining a partially circular, open aperture 110.

Referring to FIGS. 2-7, the targeting device 100 can be used to align a drill or other instrument at a desired position and trajectory with respect to various holes 82 in an internal fixation device 80, such as, for example, a proximal tibial plate. Each side-entry slot 108 of the targeting device 100 can be configured for receiving a soft tissue guide assembly 120 laterally through the side-entry slot 108. The soft tissue guide assembly 120 can include a drill guide 121, such as a hex guide, for guiding or engaging a drill or a driver, and a soft tissue protective sleeve 122 defining an internal channel 111. The soft tissue guide assembly 120 can also include an external threaded portion 124 and a knob 126 threadably movable relative to the threaded portion 124. In this manner, the targeting device 100 can be applied or removed while one or more soft tissue guide assemblies 120 with protective sleeves 122 are still attached to the fixation device 80.

In an exemplary procedure for attaching the targeting device 100 to the fixation device 80, after the fixation device 80 is inserted and placed relative to the bone, a soft tissue guide assembly 120 including a protective sleeve 122 can be inserted in one of the holes 82 at a distal end 84 of the fixation device 80, as illustrated in FIG. 3, by free-hand targeting. This procedure can be repeated for inserting another soft tissue guide assembly 120 having a protective sleeve 122 in one of the holes 82 at the proximal end 86 of the fixation device, as illustrated in FIG. 4. Holes 82 that will not be otherwise used for bone fixation can be selected for attaching the targeting device 100 to the fixation device 80.

Figure 6:
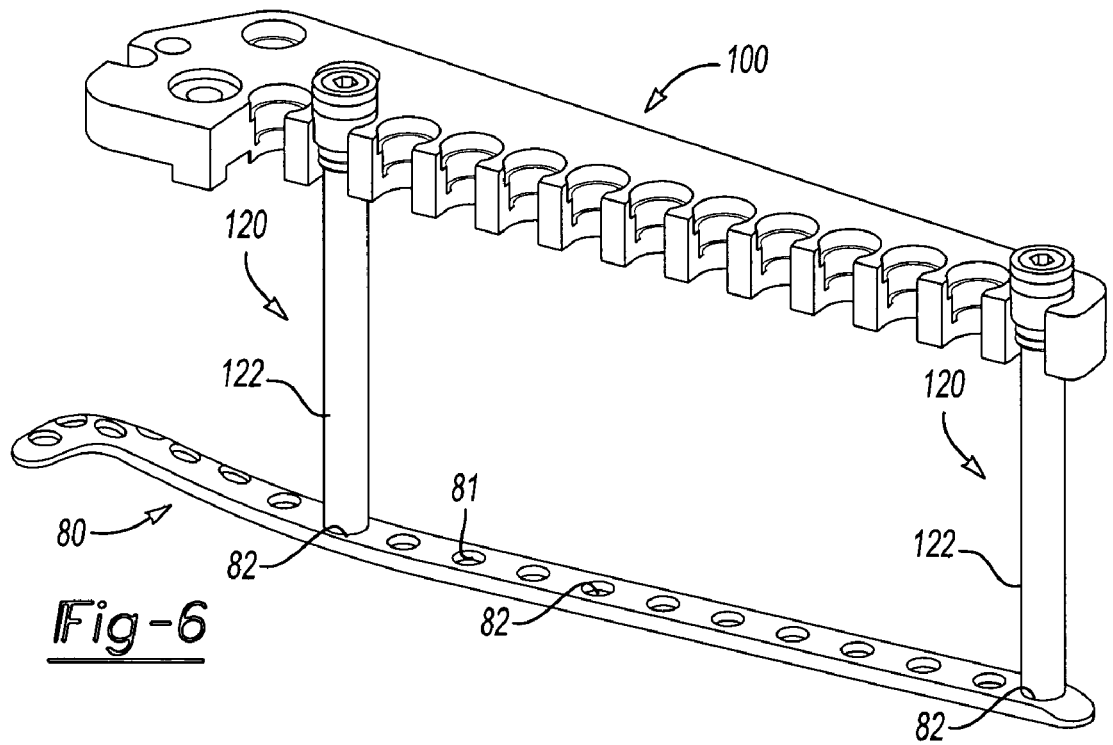
Figure 7:
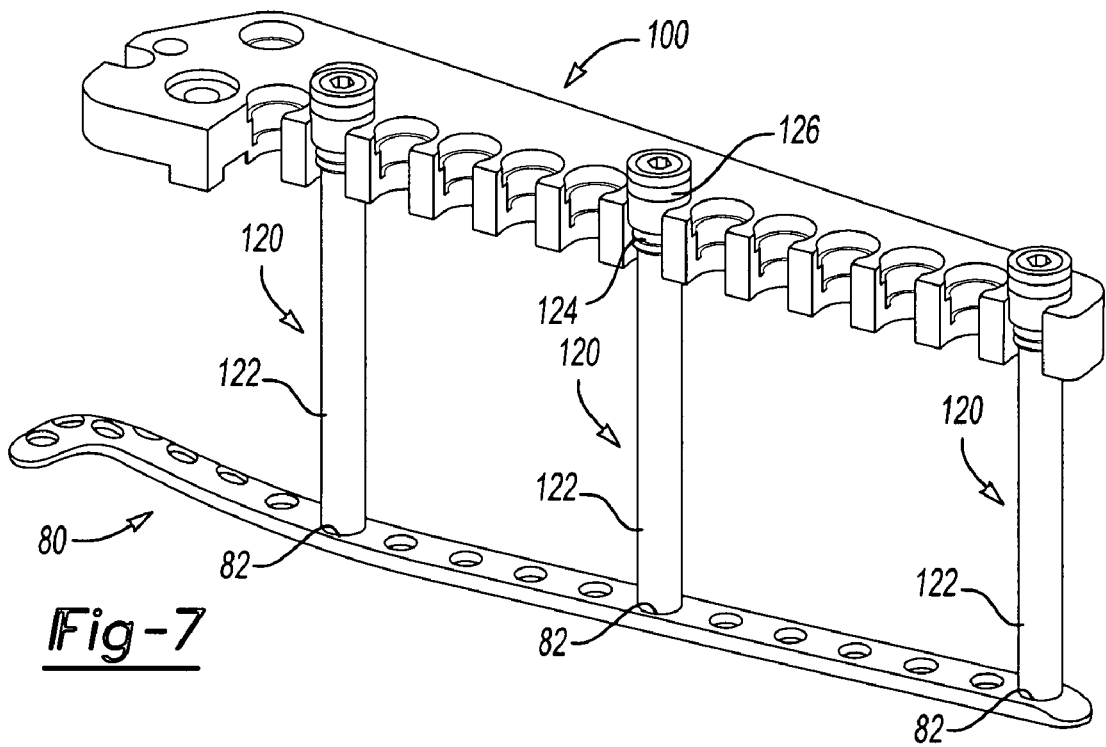
Figure 9A:
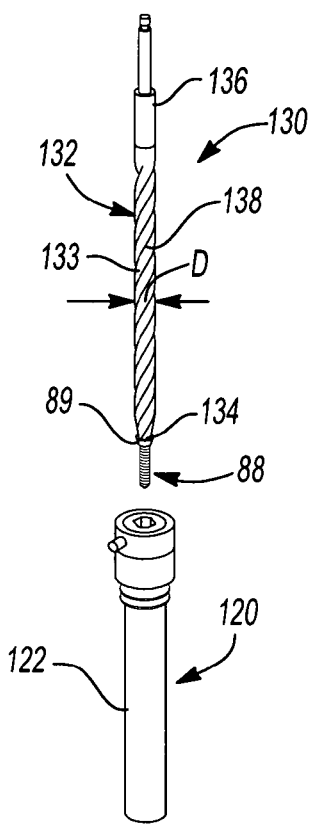
FIGS. 9A-D are a series of views illustrating insertion of a driver shaft and bone screw through an irrigation cap and into a soft tissue sleeve of the irrigation assembly according to the present teachings.
Figure 9B:
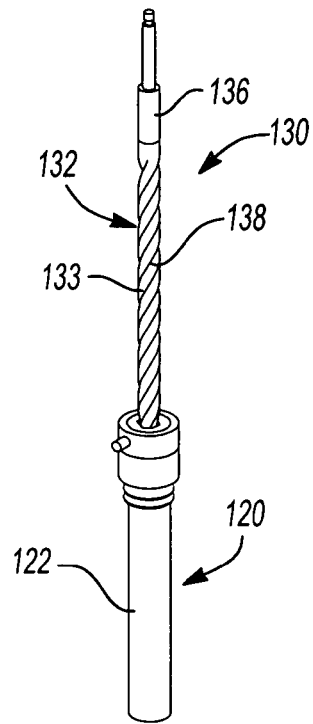
Figure 9C:
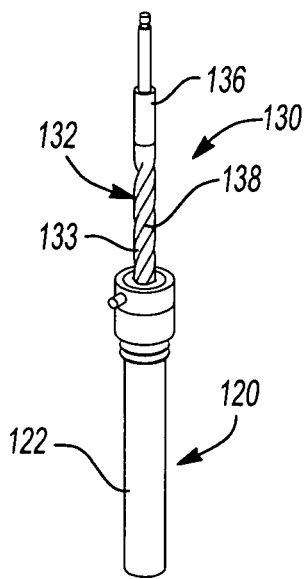
Figure 9D:
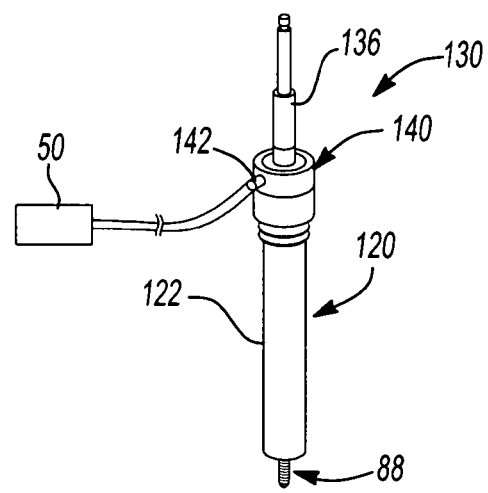

Referring to FIG. 5, the targeting device 100 can be aligned such that corresponding slots 108 are aligned with the drill guide assemblies 120 that are already attached to the fixation device 80. The targeting device 100 can then be translated laterally (e.g. in the direction of arrow A) onto the protective sleeves 122 of the soft tissue guide assemblies 120, below the threaded portions 124 of the soft tissue guide assemblies 120. Referring to FIG. 6, the targeting device 100 can be translated along the protective sleeves 122 up to the threaded portions 124. The knobs 126 can be rotated clockwise to lock the targeting device 100 to the protective sleeves 122, as illustrated in FIG. 6. Referring to FIG. 7, the targeting device 100 supported at the distal and proximal ends by two soft tissue guide assemblies 120 can be used to target, drill and insert a bone screw 88 into any of the other holes 82 of the fixation device 80 using a third soft tissue guide assembly 120.

Referring to FIG. 8, the targeting device 100 is illustrated in an application in which irrigation can be provided for reducing the increased temperature created by friction between the bone 60 and a self-drilling/self-tapping bone screw 88 during drilling, or generally between the bone 60 and any drilling instrument. The targeting device 100 can be attached to the fixation device 80 as described above. The targeting device 100 can also be cantilevered at the proximal end 102 using a proximal support 128. Irrigation can be provided by an irrigation assembly 130.

Referring to FIGS. 9A-F, the irrigation assembly 130 can include a soft tissue guide or sleeve, such as the protective sleeve 122 of the soft tissue guide assembly 120 described above, for example, and a driver 132 having a front tip 134 engageable with a head 89 of the bone screw 88, a driver shaft 133, and an opposite driver end 136 that can be coupled to a handle. The driver shaft 133 can have a substantially constant outer diameter D adapted to fit into the protective sleeve 122, and a plurality of helical grooves 138 extending along the entire length of the portion of driver shaft 133 received within the internal channel 111, between the front tip 134 and the driver end 136 of the driver 132. The grooves 138 can guide and deliver irrigation along the driver shaft 133 to the bone screw drill site. The constant diameter D can improve the accuracy and stability of the trajectory of the bone screw 88 and provide more uniform irrigation flow.

The irrigation assembly 130 can also include an irrigation cap 140 having a delivery port 142 for connection to an irrigation source 50. The irrigation cap 140 can be adapted to be removably coupled to the soft tissue guide assembly 120 adjacent the knob 126, such that the irrigation cap 140 can be optionally assembled to the soft tissue guide assembly 120 only when irrigation is needed, and can otherwise be removed. The irrigation cap 140 can include a threaded portion 143 threadably coupled to an internal threaded portion 129 of the protective sleeve 122. The irrigation cap 140 includes an axial bore 127 for allowing insertion of the driver shaft 133. It will be appreciated that other forms of connection can be used to removable attach the irrigation cap 140 to the soft tissue guide assembly 120, such as, for example, a snap-on connection, a prong-and-groove connection, or other available connections.

The irrigation assembly 130 can be used to reduce the temperature at the insertion site during a self-drilling procedure, as illustrated in FIG. 8, by pumping irrigation fluid through the delivery port 142 into the protective sleeve 122 while the driver shaft 133 is rotated to drive the self-drilling bone screw 88 into the bone 60. As the driver shaft 133 rotates, the irrigation fluid is guided along the irrigation grooves 138 and out of the protective sleeve 122 on to the insertion site of the bone screw 88. In other applications, the irrigation assembly 130 can be used to provide irrigation at a drill site when drilling is performed directly by another drilling or reaming device. The irrigation fluid can be removed by a separate aspiration device.

Referring to FIGS. 10-15, a temporary fixator 150 according to the present teachings is illustrated. The temporary fixator 150 can include a tubular component 152 and a shaft 154 that can be received within the tubular component 152 and coupled thereto. The shaft 154 can include a first threaded portion 156 terminating at a bone-gripping tip 158, an unthreaded portion 162 and a second threaded portion 155 of larger diameter. The tip 158 can be self-tapping and include one or more cutting flutes 160. The shaft 154 and or the first threaded portion 156 can be provided in various lengths for use in unicortical fixation, as illustrated in FIGS. 11, 13 and 15C, or in bicortical fixation, as illustrated in FIGS. 12, 43 and 15B.

Figure 10:
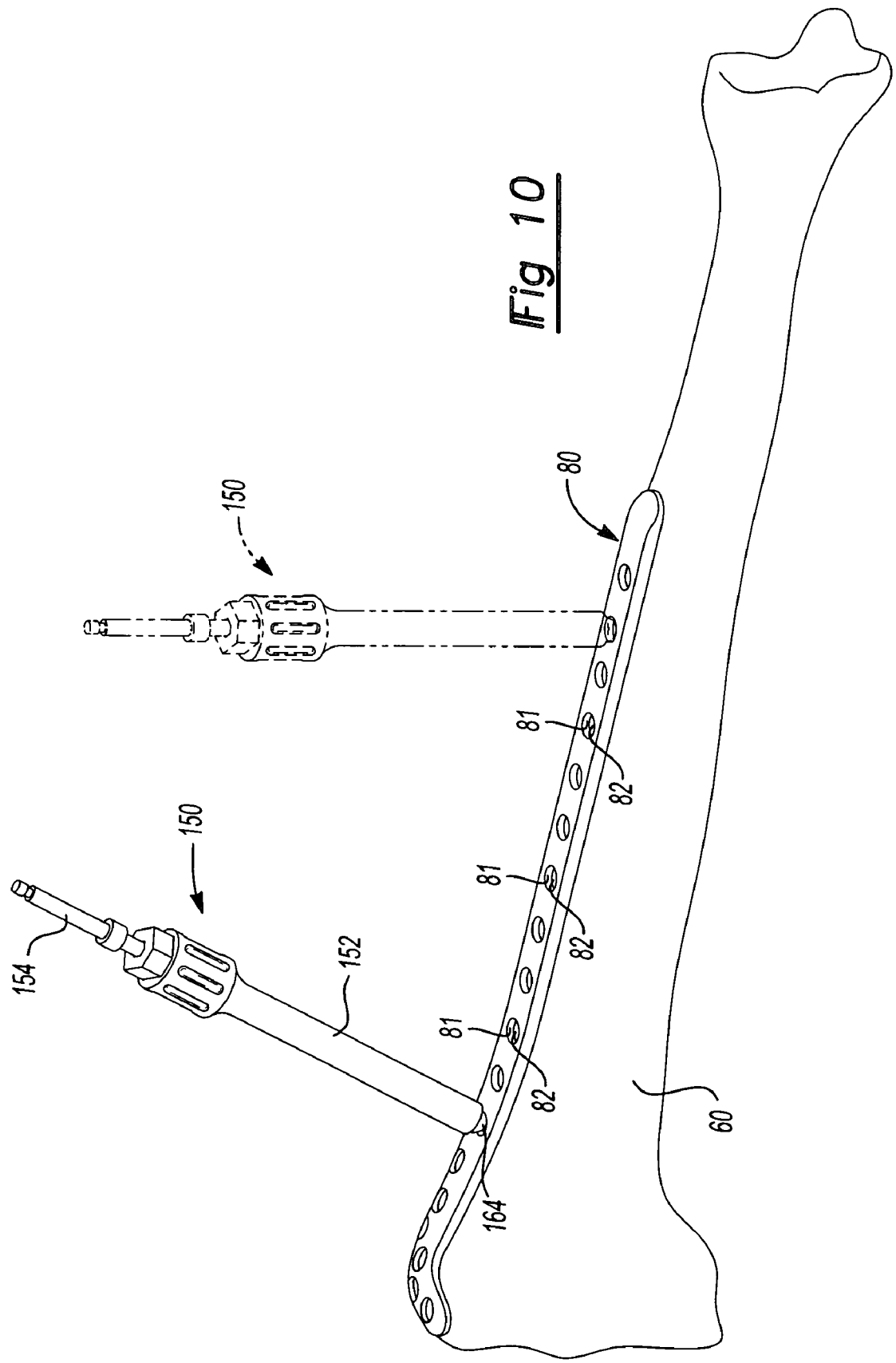
FIG. 10 is an environmental view of a temporary fixator according to present teaching shown in use with a fixation device for a bone.

FIGS. 11 and 12 illustrate the temporary fixator 150 in use with a soft tissue protective sleeve 122. The tubular component 152 can include a spherical or otherwise rounded or shaped tip 164 at an end adjacent to the bone-gripping tip 158 of the shaft 154, as assembled. The spherical tip 164 is adapted to interface in contact with an inner wall 81 of a spherical or otherwise rounded or shaped hole 82 in a fixation device 80, as illustrated in FIG. 10. The tubular component 152 can include a gripping portion 157 with internal threading for rotational coupling to the second threaded portion 155 of shaft 154.

Referring to FIG. 10, the temporary fixator 150 can be used to pull/push a bone fragment or bone portion 60 and the fixation device 150 toward one another. In use, the shaft 154 of the temporary fixator 150 can be driven into the bone 60 through the hole 82 of the fixation device 80 to a depth appropriate for unicortical or bicortical fixation, when the corresponding unicortical or bicortical shaft 154 is used. The tubular component 152 can be threadably rotated about the shaft 154, such that the tubular component 152 advances relative to the shaft 154 toward the fixation device 80 such that the spherical tip 164 can push against the inner wall 81 of the hole 82, bringing the bone 60 and the fixation device 80 toward one another. The interfacing of the spherical tip 164 and the inner wall 81 of the spherical hole 82 allows adjustment of the relative position of the fixation device 80 on the bone 60 in any direction, as illustrated in FIG. 15, in which a second temporary fixator 150 is shown in phantom lines to illustrate two exemplary orientations.

It will be appreciated that the targeting device 100, the irrigation assembly 130, and the temporary fixator 150 can be provided as an instrument kit in various sizes, and can be used together or separately as determined by the operation surgeon in a particular application.

The foregoing discussion discloses and describes merely exemplary arrangements and uses of the present teachings. One skilled in the art will readily recognize from such discussion, and from the accompanying drawings and claims, that various changes, modifications and variations can be made therein without departing from the spirit and scope of the invention as defined in the following claims.

What is claimed is:

1. An instrument assembly for internal bone fixation comprising:
   an internal fixation device attachable to a bone, the fixation device including a first hole defining a spherically shaped inner wall;
   a driver having a driver shaft, a portion of the driver shaft including helical irrigation grooves, the driver shaft having a front tip engageable with a head of a bone screw;
   a temporary fixator including a tubular component and a fixator shaft with a bone-gripping tip received in the tubular component, the tubular component having a spherical tip rotatably contacting the inner wall of the first hole of the internal fixation device at any orientation relative to the internal fixation device;
   a soft tissue sleeve having an internal channel configured to receive selectively the driver and the temporary fixator;
   an irrigation cap having an axial bore, the irrigation cap selectively and removably connectable to the soft tissue sleeve when the driver is received in the internal channel, the driver shaft passing through the axial bore, the irrigation cap having a delivery port for connection to an irrigation source; and
   a targeting device having a plurality of side-entry slots adapted to receive the soft tissue sleeve sideways, wherein the soft tissue sleeve includes an externally threaded portion and a knob for securing the soft tissue sleeve in one of the side-entry slots of the targeting device.

2. The instrument assembly of claim 1, in combination with a bone screw.

3. The instrument assembly of claim 2, wherein the bone screw is a self-tapping bone screw.

4. The instrument assembly of claim 1, wherein the internal fixation device includes a plurality of holes including the first hole and wherein the plurality of the side-entry slots correspond to the plurality of holes in the internal fixation device.

5. The instrument assembly of claim 1, wherein the fixator shaft is threadably coupled with a portion of a longitudinal bore of the tubular component.

6. The instrument assembly of claim 1, wherein the knob includes an internally threaded portion couplable to an externally threaded portion of the irrigation cap.

7. The instrument assembly of claim 1, wherein the portion of the driver shaft with the irrigation grooves is insertable in the internal channel of the soft sleeve and has a substantially constant diameter.

* * * * *